(12) United States Patent
Ziegler et al.

(10) Patent No.: US 8,479,730 B2
(45) Date of Patent: Jul. 9, 2013

(54) INHALER DEVICE

(75) Inventors: Dominik Ziegler, Basel (CH); Grant Smetham, Cambridge (GB); Mauro Citterio, Osnago (IT)

(73) Assignee: Novartis AG, Basil (CH)

( * ) Notice: Subject to any disclaimer, the term of this patent is extended or adjusted under 35 U.S.C. 154(b) by 1248 days.

(21) Appl. No.: 11/568,466

(22) PCT Filed: May 12, 2005

(86) PCT No.: PCT/EP2005/005182
§ 371 (c)(1),
(2), (4) Date: Feb. 2, 2007

(87) PCT Pub. No.: WO2005/113042
PCT Pub. Date: Dec. 1, 2005

(65) Prior Publication Data
US 2007/0295332 A1    Dec. 27, 2007

(30) Foreign Application Priority Data
May 13, 2004   (GB) .................................. 0410712.4

(51) Int. Cl.
*A61M 15/00* (2006.01)
*A61M 16/00* (2006.01)
(52) U.S. Cl.
USPC ............. 128/203.21; 128/203.12; 128/205.21
(58) Field of Classification Search
USPC ............... 128/203.15, 12, 21, 205.21, 202.27
See application file for complete search history.

(56) References Cited

U.S. PATENT DOCUMENTS

| 3,931,671 A | 1/1976 | Dittmann |
| 3,991,761 A | 11/1976 | Cocozza et al. |
| 4,249,526 A | 2/1981 | Dean et al. |
| D355,029 S | 1/1995 | Kinneir et al. |

(Continued)

FOREIGN PATENT DOCUMENTS

| CA | 2064860 | 3/2002 |
| EP | 0 333 334 A | 9/1989 |

(Continued)

OTHER PUBLICATIONS

International Search Report, PCT/EP2005/005182 (Jul. 22, 2005).

(Continued)

*Primary Examiner* — Justine Yu
*Assistant Examiner* — Colin W Stuart
(74) *Attorney, Agent, or Firm* — Michael J. Mazza

(57) ABSTRACT

An inhaler device (1) for powdered medicaments. The device (1) has a body (5) that has a recess (50) for holding a capsule containing a powdered medicament to be inhaled, at least one air passage (90) that is tangentially disposed to the recess (50), and a mouthpiece (30) that includes a coaxially disposed inhalation passage (70) that communicates with the recess (50) of the body (5). The body (5) has a pair of opposed spring (105) biased push-buttons (40) that each include at least one piercing element (95) for piercing the capsule when loaded in the recess (50). The medicament is released from the pierced capsule when air is drawn through the air passage(s) (90) into the recess (50) and swirled about therein. The mouthpiece (30) is pivotally attached to the edge of the body (5) so that it is pivotable between an open loading position and a closed dispensing position about an axis that is perpendicular to the longitudinal axis of the inhaler (1).

12 Claims, 3 Drawing Sheets

U.S. PATENT DOCUMENTS

| | | | |
|---|---|---|---|
| 5,522,383 A | 6/1996 | Calvert et al. | |
| 5,685,294 A * | 11/1997 | Gupte et al. | 128/203.15 |
| 5,797,391 A * | 8/1998 | Cook et al. | 128/203.15 |
| 5,947,118 A | 9/1999 | Hochrainer et al. | |
| 6,092,522 A * | 7/2000 | Calvert et al. | 128/203.21 |
| 6,240,918 B1 * | 6/2001 | Ambrosio et al. | 128/203.15 |
| 6,550,477 B1 * | 4/2003 | Casper et al. | 128/203.21 |
| 2003/0000523 A1 * | 1/2003 | Citterio | 128/203.15 |
| 2005/0279357 A1 * | 12/2005 | Wachtel | 128/203.15 |

FOREIGN PATENT DOCUMENTS

| | | |
|---|---|---|
| EP | 0911047 | 4/1999 |
| EP | 1270034 | 6/2006 |
| EP | 1467787 | 6/2006 |
| GB | 1485163 | 9/1977 |
| JP | 10-234827 | 9/1998 |
| WO | WO 9102558 | 3/1991 |
| WO | WO 9119524 | 12/1991 |
| WO | 94/19041 | 9/1994 |
| WO | WO 0075114 | 12/2000 |
| WO | WO 0200679 | 1/2002 |
| WO | WO 2004016601 | 2/2004 |
| WO | WO 2004096800 | 11/2004 |
| WO | WO 2005000815 | 1/2005 |

OTHER PUBLICATIONS

Written Opinion, PCT/EP2005/005182 (Nov. 14, 2006).
Bibliographic Data: WO 91/02558.

* cited by examiner

INHALER DEVICE

The present invention relates to an inhaler, particularly for use in delivering medicaments in powdered form that are useful for treating respiratory diseases such as asthma and chronic obstructive pulmonary disease.

A variety of dry powder inhaler devices (DPIs) are known in the field but they are not entirely satisfactory to use or manufacture and thus can be improved.

In a first aspect the present invention relates to an inhaler device for powdered medicaments that comprises: a body that has a recess for holding a capsule containing a powdered medicament to be inhaled; at least one air passage that is tangentially disposed to the recess; a mouthpiece that includes a coaxially disposed inhalation passage that is adapted to communicate with the recess of the body; and capsule-piercing means on said body for piercing the capsule when loaded in the recess so that the medicament is released when air is drawn through the air passage(s) into the recess and swirled about therein; the inhaler being characterised in that the capsule-piercing means comprises a pair of opposed spring biased push-buttons that each include at least one piercing element and the mouthpiece is pivotally attached to the edge of the body so that it is pivotable between an open loading position and a closed dispensing position about an axis that is perpendicular to the longitudinal axis of the inhaler.

Preferably the piercing element is a needle or sharpened pin.

Preferably the recess is formed to allow the capsule to spin within the recess about the longitudinal axis of the inhaler.

Preferably the body comprises two or more interlocking body portions that secure the mouthpiece to the edge of the body.

Preferably the capsule contains a powdered medicament that is suitable for the treatment of asthma or chronic obstructive pulmonary disease by pulmonary inhalation.

In a second aspect the present invention relates to the use of an inhaler device as described above for the administration of a medicament that is suitable for the treatment of asthma or chronic obstructive pulmonary disease by pulmonary inhalation.

Throughout this specification and in the claims that follow, unless the context requires otherwise, the word "comprise", or variations such as "comprises" or "comprising", will be understood to imply the inclusion of a stated integer or group of integers but not the exclusion of any other integer or group of integers.

The inhaler of the present invention shall now be described with reference to the preferred embodiment of the device that is illustrated in the accompanying drawings.

Figure 1:
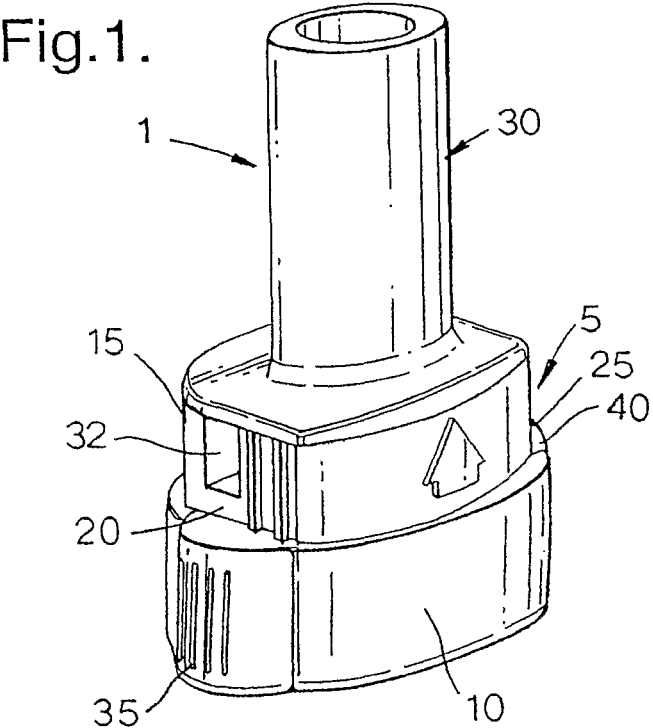
FIG. 1 is a front perspective view from one side of a preferred embodiment of the inhaler device of the present invention with the mouthpiece in its closed position.

The preferred embodiment of the inhaler device 1 of the present invention shown in FIG. 1 has a body 5 that has a front 10, a back 15, a first side 20 and a second side 25. The body 5 is formed from two interlocking body portions. The device 1 has a mouthpiece 30 that is pivotally attached to the back 15 of the body 5 and can be moved between an open position and a closed position. In FIG. 1 the mouthpiece 30 is in its closed position. The device also has a pair of air inlets 32. A pair of push-buttons 35 and 40 protrudes from the sides 20 and 25 of the body 5, whose function is explained below.

Figure 2:
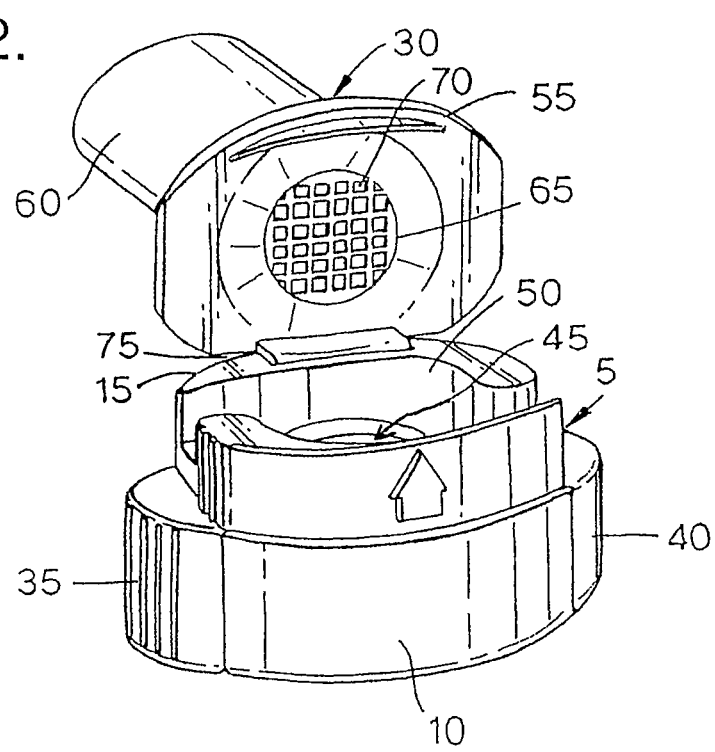
FIG. 2 is a front perspective view from one side of the inhaler shown in FIG. 1 with the mouthpiece in its open position.

FIG. 2 shows the preferred embodiment of the inhaler 1 with the mouthpiece 30 in its open position. When the mouthpiece is in its open position the user can load a capsule 33 (shown in phantom FIG. 4) containing a medicament into a capsule chamber 45 that is formed within a recess 50 in the body 5. The recess 50 has a circular cross-section for a purpose that is described below.

The mouthpiece 30 comprises a flange 55 and a tube 60. The flange 55 has a perforated plate or grid 65 that provides access to a coaxially disposed inhalation passage 70 that is formed within the tube 60.

The tube 60 of the mouthpiece can be any practical length however it is generally desirable to keep its length to a minimum as this reduces the area upon which powder can deposit and accumulate on the inhalation passage 70. This also helps to minimise the need for cleaning the device. The tube 60 is preferably substantially cylindrical and the cross-section of the inhalation passage 70 formed therein is preferably substantially round or substantially ellipsoidal so that in use the air that is swirling in the recess and carrying the medicament continues to swirl as it passes through the inhalation passage 70 and into the user's mouth.

The mouthpiece is pivotally attached to the back 15 of the body 5 by a hinge member 75. The hinge is formed to allow the mouthpiece to be moveable between its open position and its closed position about an axis that is perpendicular to the longitudinal axis of the inhaler. By hinging the mouthpiece to the body of the inhaler in that way the user can simply and conveniently open the device to load it with a capsule by gripping the body 5 with one hand, for example by placing a thumb on the front 10 of the body 5 and a forefinger on the back 15 of the body 5, and then pushing the tube 60 of the mouthpiece 30 backwards using the other hand, or perhaps the chin or even some stationary object such as a shelf or table. This construction avoids many of the real difficulties that some users experience when trying to open commercially available inhalers. This is especially true for users who are old, fragile, disabled or for some other reason have impaired dexterity that makes it difficult or perhaps even impossible for them to grip certain inhalers or to use inhalers that require a swivel or some other twisting action to be opened.

The hinge is preferably formed to permit the mouthpiece to be pivoted without the need to apply an excessive torque but also to avoid or at least substantially minimise any gaps between the flange 55 of the mouthpiece 30 and the body 5 when the mouthpiece is in its closed position. The hinge provides a secure attachment so that the mouthpiece is not readily detachable from the body. This may be achieved by trapping the hinge within the two interlocking body portions (not shown). This is particularly important when users lack fine motor skills in their hands. It also serves to prevent the mouthpiece being lost.

Figure 3:
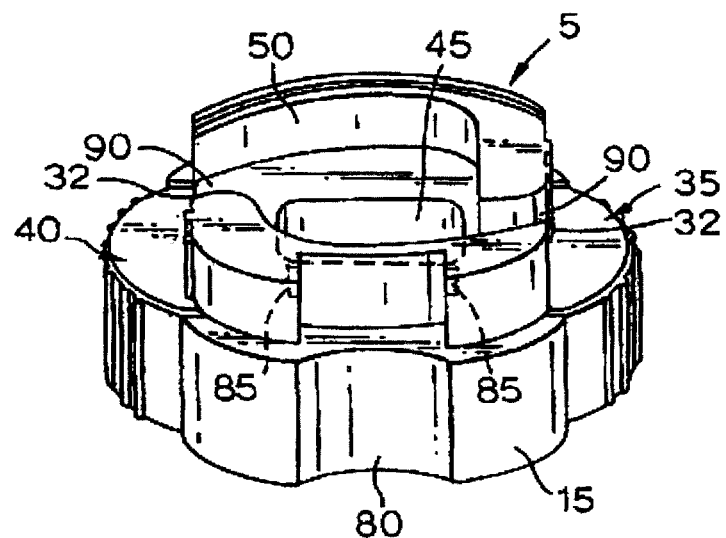
FIG. 3 is a back perspective view of the body of the same inhaler with the mouthpiece removed to show the internal construction of the body.

The internal construction of the body 5 is best seen in FIG. 3. This is a back perspective view showing the capsule chamber 45 with the recess 50. The back 15 of the body 5 has a groove 80 that helps the user to distinguish the back of the device from the front of the device. The body has a pair of opposed axle slots 85 that accommodates hinge axles (not shown) that project from the hinge member 75 of the mouthpiece 30.

A pair of air passages 90 is formed between the body 5 and the flange 55 of the mouthpiece 30 (when in its closed dispensing position) that communicate between the air holes 32 on the external surface of the device and the recess 50 within the device. These air passages 90 are tangentially disposed to the recess 50 for a purpose that is described below.

In use the user moves the mouthpiece 30 from its closed position (seen in FIG. 1) to its open position (seen in FIG. 2) as described above and places a capsule (not shown) containing a powdered medicament to be administered in the capsule chamber 45 of the recess 50. Suitable indicia may be provided on the device to indicate to the user how the mouthpiece can be moved to its open position and where the capsule should be placed. The user then moves the mouthpiece back to its closed position ready for dispensing the medicament. The user presses both push-buttons 35 and 40 substantially simultaneously to activate a capsule piercing mechanism. This mechanism is illustrated in FIG. 4.

Figure 4:
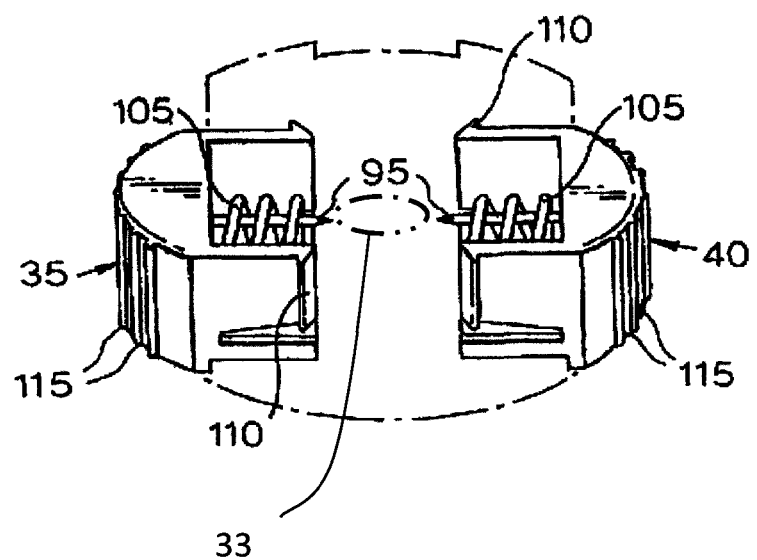
FIG. 4 is a front perspective view of the body of the inhaler with the body shown in phantom outlines to show the capsule piercing mechanism.

As seen in FIG. 4, the capsule piercing mechanisms comprises a pair of needles or sharpened pins 95 that project inwardly from the push-buttons 35 and 40. The tips are preferably shaped like hypodermic needles and may be bevelled (i.e. sliced at an angle) or symmetrically pointed to pierce the capsule cleanly and with minimal resistance. The opposed orientation of the needles serves to restrict the movement of the capsule in the capsule chamber during the piercing action and thus ensures a clean and effective perforation. The shape of the tips can also assist in restricting the movement of the capsule in the capsule chamber. For example when the tips of the pins are bevelled such that the bevelled surface faces the floor of the capsule chamber 45, the capsule will tend to be pushed towards the floor of the capsule chamber 45 as the pins penetrate the capsule. Each push-button 35/40 is transversely slidable within a gallery (not shown). In each case the push-button is urged outwards by a spring 105 that is constrained against a bush (not shown). The spring ensures the pins 95 retract from the perforated capsule when the user is no longer applying pressure to the push-buttons 35 and 40. Each push-button has a pair of shoulders 110 that abuts an inner wall of respective gallery to prevent the push-button being able to slide out of the gallery completely. Gripping elements 115 are provided on the push-buttons to assist the user to retain a good grip on the push-buttons while pushing them together to pierce the capsule.

Once the capsule has been pierced by the needles 95 the medicament contained therein is available to be administered by pulmonary inhalation. The user should release the push-buttons to allow the needles 95 to retract from the pierced capsule and then grip the body of the device once again, for example by once again placing a thumb on the front 10 of the body and a forefinger on the back 15 of the body. Users administer the medicament by breathing out fully, inserting the mouthpiece 30 into the mouth, sealing placing their lips and teeth around the mouthpiece and inhaling quickly and deeply. This action draws surrounding air into the device through the air inlets 32, along the air passages 90, and into the recess 50. The air passages 90 are positioned substantially tangentially with respect to the recess 50 so this rush of air into the recess 50 forms a vortex in the recess 50. This vortex in the recess lifts the perforated capsule out from the capsule chamber 45 and causes the capsule to spin rapidly about the longitudinal axis of the inhaler. The recess 50 has a substantially circular cross-section to accommodate the spinning capsule. The length of the capsule is slightly less than the diameter of the recess 50 so there are repeated impacts between the ends of the capsule and the side wall of the recess 50, which causes the powdered medicament from within the capsule to be drawn out through the perforations in the ends of the capsule, this being assisted by the spinning motion of the capsule itself. The powdered medicament is entrained with the air passing through the perforated plate 65 and along the inhalation passage 70 of the mouthpiece 30. The walls that define these passages, recesses and tube are formed with smooth curves to minimise air resistance and thereby minimise the effort that is required of the user to inhale the medicament. The perforated plate or grid 65 prevents the capsule being inhaled up the tube 60.

If necessary this inhalation action is repeated. When the capsule has been spent, which is more easily seen with the capsule casing is transparent, the user moves the mouthpiece from its closed (dispensing) position to its open (loading) position and discards the spent capsule. The device is then ready to be reloaded with a fresh capsule containing the desired medicament and reused.

The preferred embodiment of the device has a removable cap 120, which has a front 125 and a back 130. This is shown in FIGS. 5 and 6.

Figure 5:
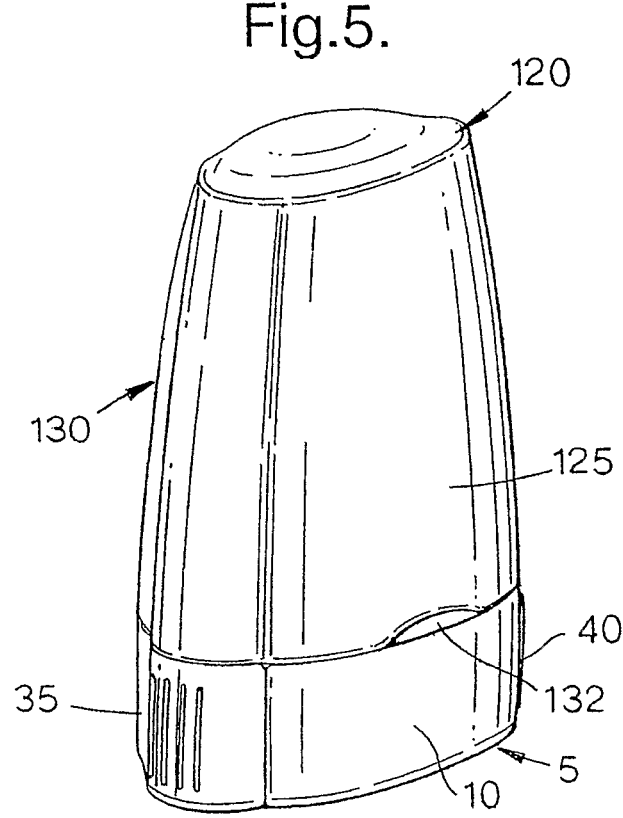
FIG. 5 is a front perspective view of the inhaler with a removable cap fitted over the mouthpiece and the upper part of the body of the inhaler.

As seen in FIG. 5, the cap 120 is formed to snap fit to the body 5 and completely cover the mouthpiece 30 and upper part of the body 5. A finger access recess 132 is formed by providing indentations in the lower edge of the front 125 of the cap 120 and, if desired, the front 10 on the body 5. This gives the user a visual and tactile cue to pull the cap 120 from the body 5 by gripping the body in one hand and inserting a finger, most conveniently a thumb, of the other hand into the finger access recess 132 and gently prising the cap 120 away from the body 5.

Figure 6:
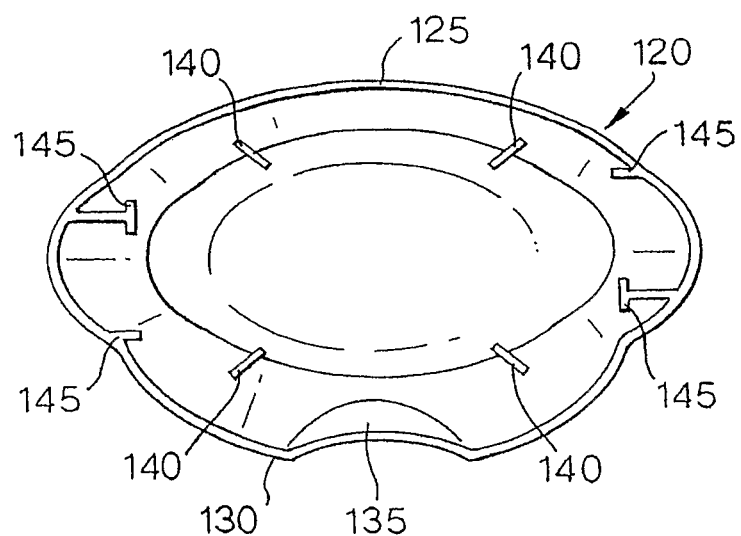
FIG. 6 is an underneath plan view of the removable cap.

As seen in FIG. 6, which is an underneath plan view of the cap 120, the back 130 of the cap 120 includes a grooved area 135 that helps the user to distinguish the back of the device from the front of the device and encourage the user to orient the device in the manner that is most convenient to use it. This is especially important when that user is visually impaired. The grooved area 135 of the cap 120 is contoured to meet and complement the groove 80 of the body 5.

If desired, a set of mouthpiece guides 140 is provided on the inner surface of the cap 120 that engages the tube 60 of the mouthpiece 30 when the cap 120 is placed over the mouthpiece 30 and the body 5 of the device. If desired, a set of ribs 145 is provided on the inner surface of the cap 120 adjacent its mouth that engages the body 5 of the inhaler when the cap 120 is placed on the device. The mouthpiece guides 140 and the ribs 145 serve to stiffen the cap and help to prevent the cap being unintentionally separated from the body, for example during storage or transportation. This is important as many people who use inhalers carry them with them wherever they go, often in some sort of bag together with a variety of other things. The cap is provided with smooth contours with this in mind.

The inhaler device of the present invention can be made of any suitable material, for example a tough plastics material such as acrylonitrile-butadiene-styrene (ABS), methyl-methacrylate-acrylonitrile-butadiene-styrene (MABS) or an anti-static material. If desired, the material is substantially transparent to help the user to more readily see and understand how the device works. This encourages users to use the device in the correct way and continue to use the device in that manner for the full term of their treatment, i.e. increase compliance.

The capsule for use in the inhaler device of the present invention contains a powdered medicament that is suitable for inhalation. The medicament is preferably suitable for the treatment of asthma or chronic obstructive pulmonary disease, for example one or more bronchodilators, anti-inflammatories or combinations thereof. Preferred bronchodilators include beta-2 adrenoceptor agonists such as albuterol (salbutamol), salmeterol, formoterol, and pharmaceutically acceptable salts thereof, and compounds (in free or salt or solvate form) of formula I of WO 00/75114 or WO 04/16601, which are incorporated herein by reference. For example, WO 00/75114 discloses the bronchodilator (R)-5-[2-(5, 6-diethyl-indan-2-ylamino)-1-hydroxyethyl]-8-hydroxy-1H-quinolin-2-one having the structure shown by formula I below:

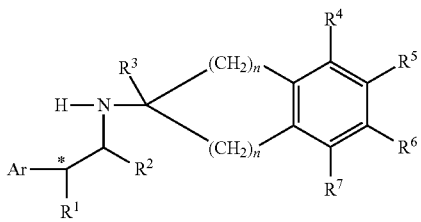

in free, salt or solvate form, wherein Ar is a group of the formula IIIa:

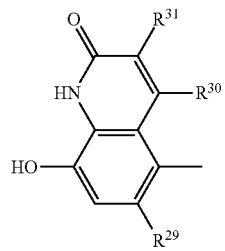

in which $R^{29}$, $R^{30}$ and $R^{31}$ are each H, $R^1$ is OH, $R^2$ and $R^3$ are each H, n is 1, $R^4$ and $R^7$ are each H, $R^5$ and $R^6$ are each $CH_3CH_2$— and the carbon atom marked with an asterisk* has the R configuration. Preferred, antimuscarinic agents include ipratropium bromide, oxitropium bromide, tiotropium, glycopyrrolate, and pharmaceutically acceptable salts thereof, and compounds (in salt or zwitterionic form) of formula I of WO 04/96800 or WO 05/00815, which are incorporated herein by reference. Preferred anti-inflammatory drugs include steroids, in particular glucocorticosteroids such as budesonide, beclomethasone dipropionate, fluticasone propionate, ciclesonide or mometasone furoate, or steroids described in WO 02/00679, which is incorporated herein by reference.

The foregoing description describes an inhaler device and a preferred embodiment thereof. In practising the invention, it is to be understood that the use and construction of the various parts can be modified to meet specific requirements.

The invention claimed is:

1. An inhaler device for powdered medicaments, the inhaler device comprising:
   a body having a recess for holding a capsule containing a powdered medicament to be inhaled, the recess formed to allow the capsule to spin within the recess about a longitudinal axis of the inhaler;
   at least one air passage that is tangentially disposed to the recess;
   a mouthpiece including a coaxially disposed inhalation passage that is adapted to communicate with the recess of the body; and
   capsule-piercing means on said body for piercing the capsule when loaded in the recess so that the medicament is released when air is drawn through the at least one air passage into the recess and swirled about therein;
wherein the capsule-piercing means comprises a pair of opposed spring biased push-buttons that each include at least one piercing element and wherein the mouthpiece is pivotally attached to a back edge of the body by a hinge so that it is pivotable between an open loading position and a closed dispensing position about an axis that is perpendicular to the longitudinal axis of the inhaler by a user applying a push force to the mouthpiece, wherein said hinge axis is parallel to an axis of actuation of said capsule-piercing means, and a back of the body further including a groove to help a user distinguish the back of the device from the front.

2. An inhaler according to claim 1, wherein the piercing element is a needle or sharpened pin.

3. An inhaler according to claim 1, wherein the inhaler further comprises a removable cap and mouthpiece guides that are provided on the inner surface of the cap and that engage the mouthpiece.

4. An inhaler according to claim 3, wherein ribs are provided on the inner surface of the cap.

5. An inhaler according to claim 1, in combination with the capsule that contains a powdered medicament.

6. An inhaler according to claim 1, wherein the hinge further comprises a pair of opposed axle slots in the body that accommodate projections from a hinge member of the mouthpiece.

7. An inhaler according to claim 1, wherein the capsule-piercing means comprises a pair of push-buttons mounted on the body so that they move along the axis of actuation.

8. An inhaler according to claim 5 wherein the powdered medicament comprises a beta-2 adrenoceptor agonist.

9. An inhaler according to claim 5 wherein the powdered medicament comprises glycopyrrolate.

10. An inhaler according to claim 5 wherein the powdered medicament comprises mometasone.

11. An inhaler according to claim 5 wherein the powdered medicament comprises a compound of the structure:

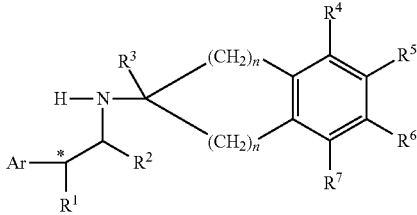

in free, salt or solvate form, wherein Ar is a group of the formula:

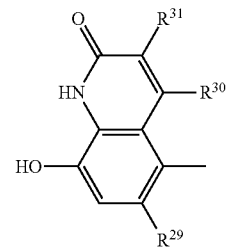

in which $R^{29}$, $R^{30}$ and $R^{31}$ are each H, $R^1$ is OH, $R^2$ and $R^3$ are each H, n is 1, $R^4$ and $R^7$ are each H and $R^5$ and $R^6$ are each $CH_3CH_2$— and the carbon atom marked with an asterisk* has the R configuration.

12. An inhaler according to claim 5 wherein the powdered medicament comprises (R)-5-[2-(5,6-diethyl-indan-2-ylamino)-1-hydroxyethyl]-8-hydroxy-1H-quinolin-2-one maleate.

* * * * *